US009999772B2

(12) United States Patent
Venkatesan

(10) Patent No.: US 9,999,772 B2
(45) Date of Patent: *Jun. 19, 2018

(54) SYSTEMS AND METHOD FOR DEEP BRAIN STIMULATION THERAPY

(71) Applicant: PACESETTER, INC., Sylmar, CA (US)

(72) Inventor: Lalit Venkatesan, Prosper, TX (US)

(73) Assignee: PACESETTER, INC., Sylmar, CA (US)

(*) Notice: Subject to any disclaimer, the term of this patent is extended or adjusted under 35 U.S.C. 154(b) by 842 days.

This patent is subject to a terminal disclaimer.

(21) Appl. No.: 14/244,596

(22) Filed: Apr. 3, 2014

(65) Prior Publication Data
US 2015/0283379 A1 Oct. 8, 2015

(51) Int. Cl.
*A61N 1/36* (2006.01)
*A61N 1/05* (2006.01)
(Continued)

(52) U.S. Cl.
CPC .......... *A61N 1/36082* (2013.01); *A61B 90/11* (2016.02); *A61N 1/0534* (2013.01); *A61B 2034/107* (2016.02); *A61B 2034/2051* (2016.02); *A61B 2090/364* (2016.02); *A61B 2090/3966* (2016.02); *A61N 1/36157* (2013.01); *A61N 1/36175* (2013.01)

(58) Field of Classification Search
CPC ... A61N 1/36082; A61N 1/0534; A61B 90/11
USPC .......................................................... 607/45
See application file for complete search history.

(56) References Cited

U.S. PATENT DOCUMENTS 7,212,110 B1    5/2007   Martin et al.
7,228,179 B2    6/2007   Van Campen et al.
(Continued)

FOREIGN PATENT DOCUMENTS

WO    2001093953 A1    12/2001
WO    2012083254 A2     6/2012

OTHER PUBLICATIONS

Dostrovsky, Jonathan O. PhD et al., "Mechanisms of Deep Brain Stimulation," Movement Disorders. 2002;17(Supp 3):S63-S68.
(Continued)

*Primary Examiner* — Kennedy Schaetzle

(57) ABSTRACT

A system and method for performing deep brain stimulation (DBS) therapy are provided. The method and system include pre-operatively acquiring at least one pre-operative image of the brain with at least one imaging sub-system and determining a location of a Nucleus Basalis of Meynert (NBM) for therapy in the at least one pre-operative image, and intra-operatively acquiring at least one intra-operative image of the brain after obtaining an access opening through the skull. The method and system further provide performing surgical planning based on the pre-operative image in the intra-operative image, advancing a lead having DBS electrodes on the lead to a target position proximate to or within the NBM area, and coupling the lead to an implantable pulse generator (IPG) configured to deliver DBS pulses through the DBS electrodes to the NBM. Further, the IPG is configured to deliver DBS pulses for treating symptoms associated with Alzheimer's disease.

20 Claims, 10 Drawing Sheets

(51) Int. Cl.
*A61B 90/11* (2016.01)
*A61B 90/00* (2016.01)
*A61B 34/10* (2016.01)
*A61B 34/20* (2016.01)

(56) References Cited

U.S. PATENT DOCUMENTS

| | | | |
|---|---|---|---|
| 7,571,007 B2 | 8/2009 | Erickson et al. | |
| 7,811,294 B2 | 10/2010 | Strommer et al. | |
| 8,343,076 B2 | 1/2013 | Sela et al. | |
| 8,957,198 B2 * | 2/2015 | Kaemmerer | A61K 9/0085 |
| | | | 536/24.5 |
| 2001/0021806 A1 * | 9/2001 | Gueziec | A61B 6/032 |
| | | | 600/425 |
| 2005/0085714 A1 * | 4/2005 | Foley | A61B 34/20 |
| | | | 600/424 |
| 2005/0245810 A1 * | 11/2005 | Khamene | G01R 33/56 |
| | | | 600/410 |
| 2005/0272991 A1 * | 12/2005 | Xu | A61B 6/032 |
| | | | 600/407 |
| 2006/0170486 A1 | 8/2006 | Tranchina et al. | |
| 2006/0173510 A1 * | 8/2006 | Besio | A61B 5/0482 |
| | | | 607/45 |
| 2007/0225553 A1 * | 9/2007 | Shahidi | A61B 5/064 |
| | | | 600/103 |
| 2008/0154331 A1 * | 6/2008 | John | A61N 1/025 |
| | | | 607/45 |
| 2009/0118787 A1 * | 5/2009 | Moffitt | A61N 1/36082 |
| | | | 607/45 |
| 2009/0326608 A1 | 12/2009 | Huynh et al. | |
| 2010/0168816 A1 * | 7/2010 | Tass | A61N 1/36082 |
| | | | 607/45 |
| 2011/0009879 A1 | 1/2011 | Derrick et al. | |
| 2011/0072657 A1 | 3/2011 | Swanson et al. | |
| 2011/0137381 A1 * | 6/2011 | Lee | A61N 1/0529 |
| | | | 607/62 |
| 2011/0313282 A1 * | 12/2011 | Frankel | A61B 8/06 |
| | | | 600/424 |
| 2012/0095531 A1 * | 4/2012 | Derbas | A61N 1/0553 |
| | | | 607/68 |
| 2012/0099770 A1 * | 4/2012 | Cagnan | A61B 19/50 |
| | | | 382/128 |
| 2013/0131753 A1 * | 5/2013 | Simon | A61N 1/36 |
| | | | 607/40 |
| 2013/0184781 A1 | 7/2013 | Eskandar et al. | |
| 2013/0231709 A1 | 9/2013 | Lozano | |
| 2014/0350635 A1 * | 11/2014 | Strother | A61N 1/375 |
| | | | 607/45 |
| 2016/0220821 A1 * | 8/2016 | O'Connell | A61N 2/006 |
| 2017/0106193 A1 * | 4/2017 | Carcieri | A61N 1/36139 |

OTHER PUBLICATIONS

Hardenacke K. et al., "Stimulate or Degenerate: Deep Brain Stimulation of the Nucleus Basalis Meynert in Alzheimer Dementia," World Neurosurg. 2013;80(3-4);S27,E35-E3.

Hemm, Simone et al., "Stereotactic implantation of deep brain stimulation electrodes: a review of technical systems, methods and emerging tools," Med Biol Eng Comput. 2010;48(7):611-624.

Laxton, A.W. et al., "Deep Brain Stimulation for the Treatment of Alzheimer Disease and Dementias," World Neurosurg. 2013;80(3-4);S27:E1-E8.

Volkmann, Jens MD et al., "Introduction to the Programming of Deep Brain Stimulators," Movement Disorders. 2002;17(Supp 3):S181-S187.

* cited by examiner

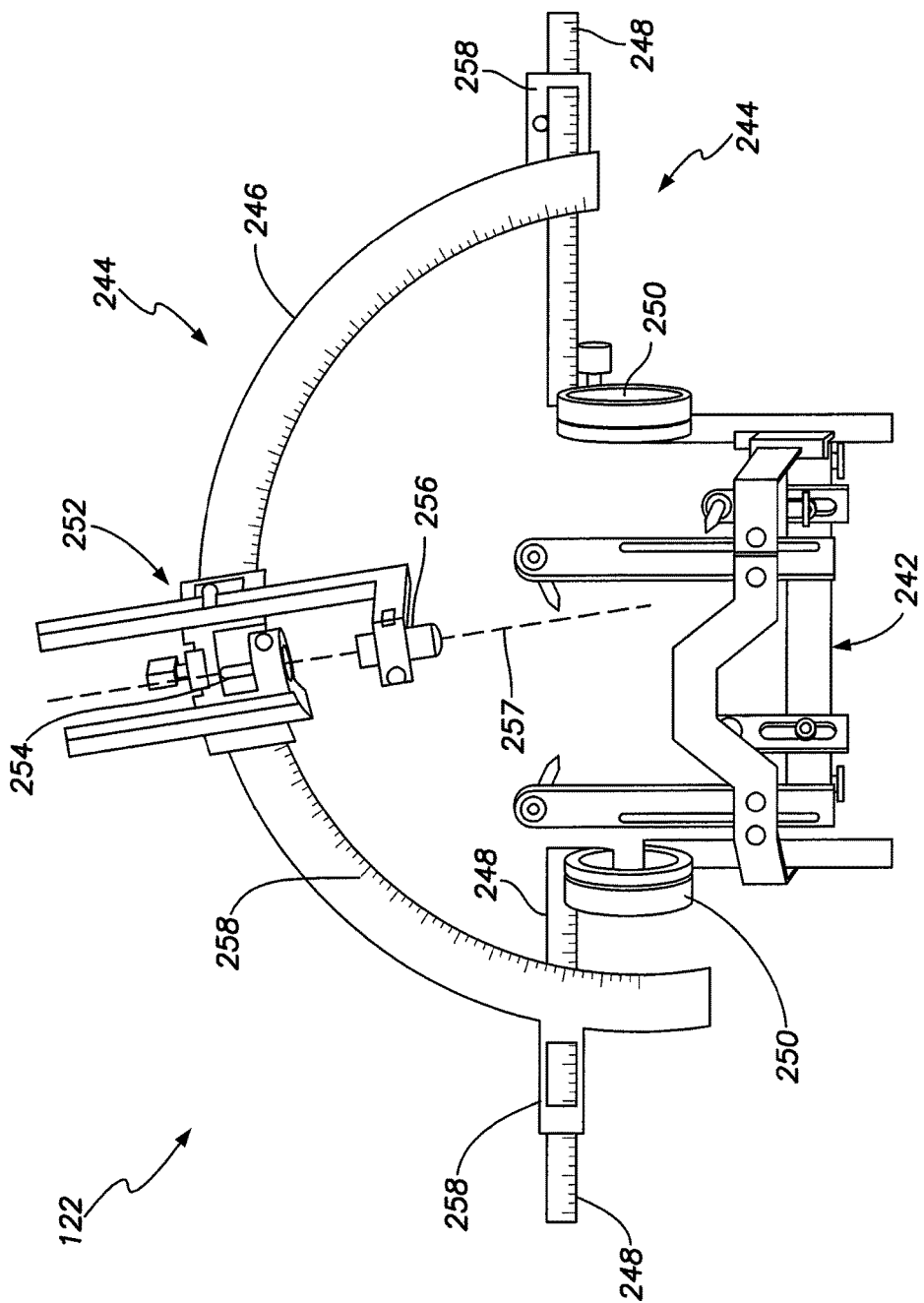

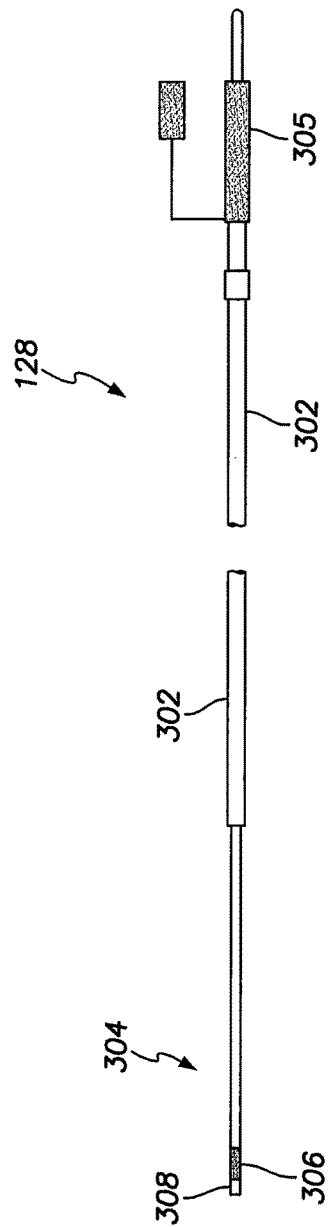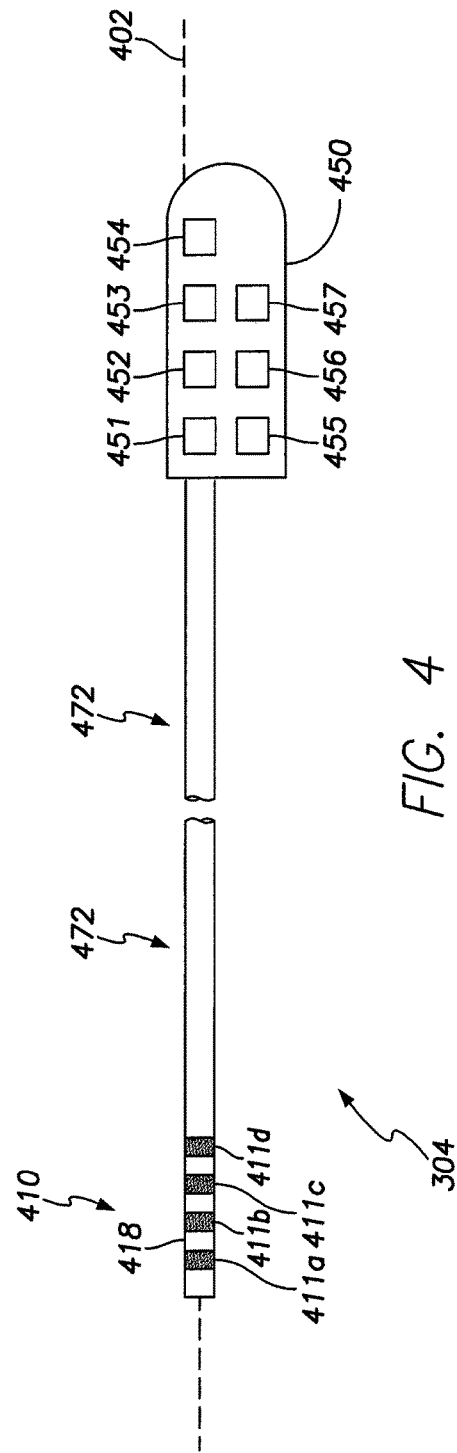

SYSTEMS AND METHOD FOR DEEP BRAIN STIMULATION THERAPY

FIELD OF THE INVENTION

Embodiments of the present disclosure generally relate to deep brain stimulation (DBS) therapy, and more particularly to treatment of symptoms associated with Alzheimer's disease (AD).

BACKGROUND OF THE INVENTION

DBS represents a therapy that has been shown to treat and relieve certain neurological disorders, such as Parkinson's disease, tremors, dystonia, psychiatric illness, and the like. In general, DBS may include electrically stimulating certain areas of the brain to alter or otherwise affect behavior to alleviate the effects of a neurological disorder. The behavioral effects of brain stimulation typically depend on a location of a stimulating electrode within the brain. For example, DBS of the Nucleus Accumbens (NAcc) has shown to reduce depression, anhedonia, and anxiety.

DBS is being used for treating cognitive disorders such as Alzheimer's Disease (AD). AD is one of the most common degenerative dementias, and is accompanied by cognitive deficits in neuropsychiatric symptoms such as depression, apathy, agitation, and the like that involve degeneration of neural circuits. There are currently two targets for DBS therapy in treating AD, specifically for improving memory, the fornix and the entorhinal cortex. The fornix as a target for DBS in the treatment of AD is described in, for example, U.S. Patent Application Publication No. 2013/0231709, entitled, "COGNITIVE FUNCTION WITHIN THE HUMAN BRAIN." DBS of the fornix has been shown to enhance neurogenesis and the release of neurotrophic factors in the hippocampus. DBS of the entorhinal cortex and the hippocampus for AD treatment are described, for example, in WO 2012/083254, entitled, "SITE SPECIFIC DEEP BRAIN STIMULATION FOR ENHANCEMENT OF MEMORY."

Nucleus Basalis of Meynert (NBM) is a group of neurons located at the base of the forebrain, anterior to the hypothalamus, and ventral to the basal ganglia adjacent to the NAcc. The NBM provides cholinergic innervation to the cerebral cortex by distributing the neurotransmitter acetylcholine (ACh) via cholinergic fibers projecting to the hippocampus and amygdala. Reduced ACh levels has been shown to impair cognitive function affecting learning and memory in a similar way as with patients diagnosed with AD.

Accordingly, a system and method is needed for DBS of the NBM to serve as a treatment for AD.

SUMMARY

In accordance with one embodiment, a method for performing deep brain stimulation (DBS) therapy is provided. The method includes pre-operatively acquiring at least one pre-operative image of the brain of a patient with at least one imaging sub-system. The method also includes determining a location of a Nucleus Basalis of Meynert (NBM) for therapy in the at least one pre-operative image, and intra-operatively acquiring at least one intra-operative image of the brain after obtaining an access opening through the skull of the patient. The method further provides, performing surgical planning based on the pre-operative image in the intra-operative image. Additionally, the method includes advancing a lead having DBS electrodes on the lead to a target position proximate to or within the NBM area, and coupling the lead to an implantable pulse generator (IPG) configured to deliver DBS pulses through the DBS electrodes to the NBM. Further, the IPG is configured to deliver DBS pulses for treating symptoms associated with Alzheimer's disease.

In an embodiment, a system for performing deep brain stimulation (DBS) therapy is described with a surgical planning (SP) workstation having an input configured to receive at least one pre-operative image of the brain of the patient with at least one imaging sub-system. The SP workstation is configured to permit the user to determine a location of a Nucleus Basalis of Meynert (NBM) for therapy in the at least one pre-operative image. The SP workstation also has an input configured to receive at least one intra-operative image of the brain after obtaining an access opening through its goal of the patient. Additionally, the SP workstation is configured to perform surgical planning based on the pre-operative image in the intra-operative image. The system also includes a lead having deep brain stimulation (DBS) electrodes on the lead. The DBS electrodes are configured to be advanced to a target position proximate to or within the NBM area. Further, the system includes an implantable pulse generator (IPG) coupled to the lead. The IPG is configured to deliver DBS pulses through the DBS electrodes to the NBM. The IPG is also configured to deliver DBS pulses for treating symptoms associated with Alzheimer's disease.

BRIEF DESCRIPTION OF THE DRAWINGS

FIG. 2 illustrates a perspective view of a stereotactic frame secured to a head of a patient in accordance with an embodiment of the present disclosure.

FIG. 3 illustrates a lateral view of a probe in accordance with an embodiment of the present disclosure.

FIG. 4 illustrates an enlarged view of an implantable DBS system in accordance with an embodiment of the present disclosure.

DETAILED DESCRIPTION

Embodiments described herein provide systems and methods for performing deep brain stimulation (DBS) therapy and/or manufacturing or using a DBS system. Embodiments described herein further provide methods for stimulating a Nucleus Basalis of Meynert (NBM) using a surgical planning (SP) work station to determine a location of the NBM from at least one pre-operative image of a brain of a patient, and for positioning a lead with DBS electrodes proximate to or within the NBM based on the pre-operative image and an intra-operative image. An implantable pulse generator (IPG) is coupled to the lead to deliver DBS pulses through the DBS electrodes for treating symptoms associated with Alzheimer's Disease (AD). In certain embodiments, the lead is positioned such that the DBS electrodes deliver DBS pulses, within an energy trajectory, to the NBM and to a Nucleus Accumbens (NAcc) for treating psychiatric symptoms. In certain embodiments, the DBS electrodes on the lead are configured to have a first and second electrodes sets.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1:
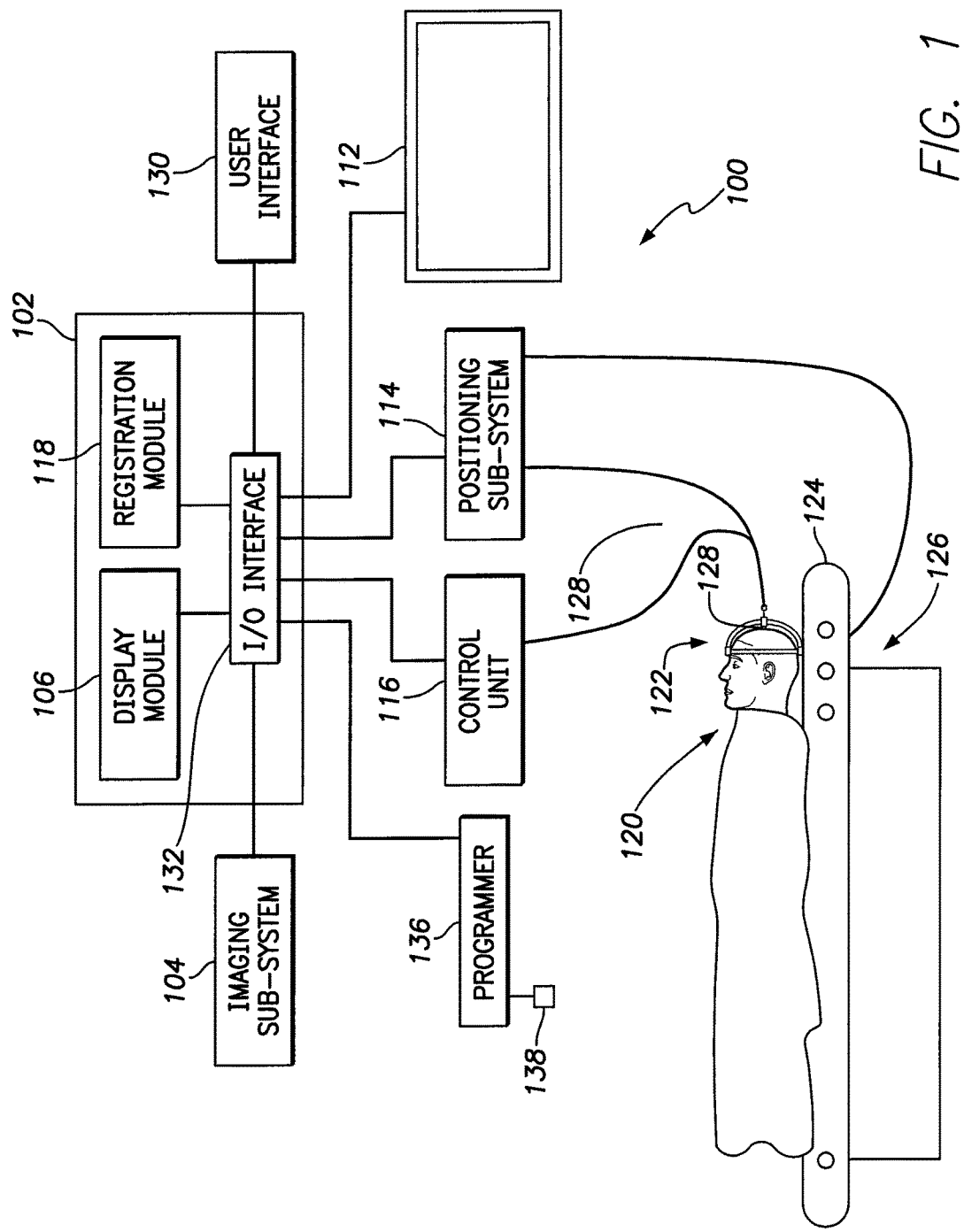
FIG. 1 illustrates a schematic diagram of a system for performing deep brain stimulation (DBS) therapy in accordance with an embodiment of the present disclosure.

FIG. 1 illustrates a schematic diagram of a system 100 for performing deep brain stimulation (DBS) therapy, according to an embodiment of the present disclosure. The system 100 may include one or more imaging sub-systems 104 configured to acquire one or more pre-operative images and one or more intra-operative images of a brain of a patient 120. The imaging sub-system 104 may include one or more of an x-ray, fluoroscope, CT, MRI, positron emission tomography (PET), ultrasound, or other such imaging systems. For example, the image sub-system 104 may include Computed Tomography (CT) imaging and Magnetic Resonance Imaging (MRI) systems. In general, the imaging sub-system 104 may include a radiation source or generator and a radiation sensor or detector.

The system 100 may also include a surgical planning (SP) workstation 102. The SP workstation 102 may include a set of input and/or output terminals within an I/O interface 132 and may contain a display module 106 and a registration module 118.

The I/O interface 132 sends/receives data or signals between the SP workstation 102 to external sub-systems or interfaces such as the imaging sub-system 104, a user interface 130, a positioning sub-system 114, a control unit 116, a programmer unit 136, and a display 112. Additionally or alternatively, the I/O interface 132 may format the data signals to the respective protocols of the destination.

For example, the I/O interface 132 may include an input configured to receive at least one pre-operative image from the imaging sub-system 104. The imaging sub-system 104 may send the pre-operative image along a serial line. The I/O interface 132 may configure the input to deserialize the line (e.g., transport to a parallel bus) to be interpreted by the SP workstation 102.

The display module 106 may be configured to display the pre-operative image and/or the intra-operative image onto the display 112 through the I/O interface 132. The display 112 may be or include a monitor, screen, television, or the like. The display module 106 allows a user (e.g., doctor, clinician) to determine the location of the NBM for DBS therapy by viewing the pre-operative image of the brain on the display 112. For example, the imaging sub-system 104 may use an MRI imaging modality to obtain the pre-operative image showing a coronel plane of a head of the patient 120. The pre-operative image is received by the display module 106 through the I/O interface 132. The display module 106 configures or adjusts a resolution, an aspect ratio, a contrast, a codec, or the like of the pre-operative image in order for the pre-operative image to be displayed on the display 112. Once the pre-operative image is on the display 112, the user may view or analyze the pre-operative image to locate the NBM. Optionally, the user may, through the user interface 130, adjust the contrast, zoom in/out on a select or predetermined coordinate, or the like of the pre-operative image shown on the display 112. The user interface 130 may be or include a handheld device having a display and input members, such as keys, a touchscreen, and/or the like. Alternatively, the interface 130 may be or include a keyboard, mouse, or touchscreen of the computer, tablet, or the like. Additionally or alternatively, the user may, through the user interface 130, overlay a graphical marker (e.g., an 'x', cross hairs) to indicate a biological structure for a DBS target such as, for example, the NBM.

The registration module 118 may be configured to register the pre-operative and intra-operative images. Optionally, the registration module 118 may merge the pre-operative and intra-operative images forming a single image to be displayed on the display 112 using a software algorithm. Additionally or alternatively, the registration module 118 may register the pre-operative and/or intra-operative images with a brain structure atlas (e.g., Talairach atlas) to aid in the identification of the DBS target.

The SP workstation 102 may be in communication with the control unit 116. The control unit 116 may include a driving mechanism controlled by the user through the user interface 130. The driving mechanism may operatively control the movement of a probe 128 relative to the patient 120. The probe 128 may be operatively connected to a stereotactic frame 122 secured to the head of the patient 120.

FIG. 2 shows a perspective view of one embodiment of the stereotactic frame 122 shown secured to the patient 120 in FIG. 1. The stereotactic frame 122 may include a circular band 242 configured to be positioned around a portion of the head of the patient 120. A positioning device 244 is secured to the circular band 242 through opposed rotatable mounts 250. The positioning device 244 may include opposed linear beams 248 coupled to the rotatable mounts 250. The position device 244 may also include a semi-circular beam 246 that is moveably secured to the opposed linear beams 248, which allows the semi-circular beam 246 to bi-directionally traverse along the opposed linear beams 248.

A platform 252 is slidably secured to the semi-circular beam 246. The platform 252 is configured to be moved to different areas by traversing the platform 252 along the semi-circular beam 244. The platform 252 may include an upper guide member 254 and a lower guide member 256. The upper and lower guide members 254 and 256 are aligned with respect to an insertion axis 257. The semi-circular beam 246 and the linear beams 248 may include scale markings 258 that are configured to provide an accurate measure of the position of the upper and lower guide members 254 and 256 relative to the platform 252, the angular position of the platform 252 relative to the semi-circular beam 246, and the rotational position of the semi-circular beam 246 relative to the circular band 242. As such, the orientation of the insertion axis 257 and any positions relative to the upper and lower guide members 254 and 256 to the circular band 246 may be correlated.

The stereotactic frame 122 shown in FIG. 2 is just one example of a frame that may be used with embodiments of the present disclosure. Various other types of frames may be used with respect to embodiments of the present disclosure. For example, the stereotactic frame may be constructed as described in FIG. 2B of application title "SYSTEMS AND METHODS FOR PERFORMING DEEP BRAIN STIMULATION" (U.S. patent application Ser. No. 14/222,301, filed Mar. 21, 2014), which is expressly incorporated herein by reference in its entirety.

The system 100 may also include an array of position sensors 126 within the vicinity of the head of the patient 120. The position sensors 126 are operatively coupled to the positioning sub-system 114. For example, the position sensors 126 may be positioned within a housing situated on or underneath a platform 124 on which the patient 120 rests. The position sensors 126 may include one or more transmitters configured to radiate a field, such as an electromagnetic field, within the vicinity of the patient 120. The field radiated by the transmitters is detected by a position detector of the probe 128, which is monitored by the positioning sub-system 114.

FIG. 3 illustrates a lateral view of the probe 128 according to one embodiment of the present disclosure. It should be noted that various other types of probe or catheter structures may be used with respect to embodiments of the present disclosure. For example, the positioning probes may be constructed as described in FIGS. 5-8 of application title "SYSTEMS AND METHODS FOR PERFORMING DEEP BRAIN STIMULATION" (U.S. patent application Ser. No. 14/222,301, filed Mar. 21, 2014), which is expressly incorporated herein by reference in its entirety. The probe 128 may be used to position one or more implantable DBS systems 304 within a predetermined implantation distance of one or more DBS targets. The probe 128 includes a guide tube 302 defining an internal passage, which the implantable DBS system 304 may traverse through. The guide tube 302 may be formed from a flexible plastic, silicone rubber, nitinol, or the like.

An enlarged illustration of an embodiment of the implantable DBS system 304 is illustrated in FIG. 4. The implantable DBS system 304 includes a DBS lead 410 on the distal end of the implantable DBS system 304 coupled to an implantable pulse generator (IPG) 450 that is adapted to generate electrical pulses, or DBS pulses. The IPG typically comprises a metallic housing that encloses a controller 451, pulse generating circuitry 452, a charging coil 453, a battery 454, far-field and/or near field communication circuitry 455, battery charging circuitry 456, switching circuitry 457, and the like. The controller 451 may include a microcontroller or other suitable processor for controlling the various other components of the DBS lead 304. Software code is typically stored in memory of the IPG 450 for execution by the microcontroller or processor to control the various components of the DBS lead 304.

Electrical pulses (e.g., DBS pulses) are generated within the IPG 450 through respective pulse generating circuitry 452 and are provided to switching circuitry 457. The switching circuitry 457 connects to outputs of the IPG 450. Electrical connectors (e.g., "Bal-Seal" connectors) within a DBS lead body 472 and/or within the IPG "header" portion of the IPG 450, as known in the art, may be employed to conduct the DBS pulses towards the DBS lead 410. The DBS lead body 472 may be electrically coupled to the IPG header portion of the IPG 450 through one or more terminals. Thereby, the DBS pulses originating from the IPG 450 are provided to the DBS lead 410. The DBS pulses are then conducted through conductors within the DBS lead 410 and applied to tissue (e.g., the DBS target) of the patient 120 via DBS electrodes 411a-d.

The DBS electrodes 411a-d may be positioned along a horizontal axis 402 of the DBS lead 410, and are angularly positioned about the horizontal axis 402 so the DBS electrodes 411a-d do not overlap. The DBS electrodes 411a-d may be in the shape of a ring such that each DBS electrode 411a-d continuously covers the circumference of the exterior surface of the DBS lead 410. Each of the DBS electrodes 411a-d are separated by non-conducting rings 418, which electrically isolate each electrode 411a-d from an adjacent electrode 411a-d. The non-conducting rings 418 may include one or more insulative materials and/or biocompatible materials to allow the DBS lead 410 to be implantable proximate to or within the DBS target. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The DBS electrodes 411a-d may be configured to emit the DBS pulse in an outward radial direction proximate to or within the DBS target. Additionally or alternatively, the DBS electrodes 411a-d may be in the shape of a split or non-continuous ring such that the DBS pulse may be directed in an outward radial direction adjacent to the DBS electrodes 411a-d. Examples of a fabrication process of the DBS electrodes 411a-d is disclosed in U.S. Patent Application Publication No. 2011/0072657, entitled, "METHOD OF FABRICATING STIMULATION LEAD FOR APPLYING ELECTRICAL STIMULATION TO TISSUE OF A PATIENT," which is expressly incorporated herein by reference.

It should be noted the DBS electrodes 411a-d may be in various other formations, for example, in a planar formation on a paddle structure as disclosed in U.S. patent application Ser. No. 14/198,260, filed Mar. 5, 2014, entitled, "PADDLE LEADS FOR NEUROSTIMULATION AND METHOD OF DELIVERYING THE SAME," which is expressly incorporated herein by reference.

The DBS lead 410 may comprise a DBS lead body 472 of insulative material about a plurality of conductors within the material that extend from a proximal end of lead 410, proximate to the IPG 450, to its distal end. The conductors electrically couple a plurality of the DBS electrodes 411a-d to a plurality of terminals (not shown) of the DBS lead 410. The terminals are adapted to receive electrical pulses (e.g., DBS pulses) and the DBS electrodes 411a-d are adapted to apply the DBS pulses to the DBS target of the patient 120. Also, sensing of physiological signals may occur through the DBS electrodes 411, the conductors, and the terminals. It should be noted that although the DBS lead 410 is depicted with four DBS electrodes 411a-d, the DBS lead 410 may include any suitable number of DBS electrodes 411a-d (e.g., less than four, more than four) as well as terminals, and internal conductors.

Additionally or alternatively, various sensors (e.g., a position detector 306, a radiopaque fiducial 308) may be located near the distal end of the DBS lead 410 and electrically coupled to terminals through conductors within the DBS lead body 472. For example, the position detector 306 may be secured to the distal end of the DBS lead 410. The position detector 306 may include one or more coils that are configured to detect the radiation field, such as an electromagnetic field, emitted by the position sensors 126 (FIG. 1). The position detector 306 may be in communication with the positioning sub-sytem 114, for example, through the communication circuitry 455 via a DBS connector 305. The position detector 306 may communicate position measurements of the position detector 306, which may be related to the radiation field strength detected by the position detector 306.

In another example, the radiopaque fiducial 308 may be secured to the distal end of the DBS lead 410 and/or the position detector 306. The radiopaque fiducial 308 may be a ball formed of platinum, titanium, or the like, which resists or absorbs relatively less electromagnetic radiation than tissue surrounding the DBS target. Thereby, when imaged by the imaging sub-system 104 (e.g., the intra-operative image) the radiopaque fiducial 308 will be more apparent and/or distinguishable from the surrounding tissue by the user when viewing the display 112. Additionally or alternatively, the radiopaque fiducial 308 may be located at various other positions of the probe 128 and/or the DBS lead body 472 along the horizontal axis 402 (e.g., at the IPG 450 header, a midpoint of the implantable DBS system 304).

Although not required for all embodiments, the DBS lead body 472 of the DBS lead 410 may be fabricated to flex and elongate upon implantation or advancing within the brain of the patient 120 towards the DBS target and movements of the patient 120 after implantation. By fabricating the DBS lead body 472, according to some embodiments, the DBS lead body 472 or a portion thereof is capable of elastic elongation under relatively low stretching forces. Also, after removal of the stretching force, the lead body 472 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 450, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 456) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 452) is provided in U.S. Patent Application Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 450. Different DBS pulses on different electrodes 411a-d may be generated using a single set of pulse generating circuitry 452 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide DBS pulse patterns that include simultaneously generated and delivered stimulation pulses through various electrodes of one or more DBS leads as is also known in the art. Various sets of parameters may define the pulse characteristics and pulse timing for the DBS pulses applied to the various electrodes 411a-d as is known in the art. Although constant current pulse generating circuitry is contemplated for some embodiments, any other suitable type of pulse generating circuitry may be employed such as constant voltage pulse generating circuitry.

The programmer unit 116 (FIG. 1) may be implemented to charge/recharge the battery 454 of the IPG 450 (although a separate recharging device could alternatively be employed) and to program the IPG 450 on the DBS pulse specifications while implanted within the patient 120. Although, in alternative embodiments separate programmer devices may be employed for charging and/or programming the implantable DBS system 304. The programmer unit 136 may be a processor-based system that possesses wireless communication capabilities. Software may be stored within a non-transitory memory of the programmer unit 136, which may be executed by the processor to control the various operations of the programmer unit 136. A "wand" 138 may be electrically connected to the programmer unit 116 through suitable electrical connectors (not shown). The electrical connectors may be electrically connected to a telemetry component (e.g., inductor coil, RF transceiver) at the distal end of wand 138 through respective wires (not shown) allowing bi-directional communication with the IPG 450. Optionally, in some embodiments, the wand 138 may comprise one or more temperature sensors for use during charging operations.

The user may initiate communication with the IPG 450 by placing the wand 138 proximate to the implantable DBS system 304 or the head of the patient 120 when implanted. Preferably, the placement of the wand 138 allows the telemetry system of the wand 138 to be aligned with the far-field and/or near field communication circuitry 455 of the IPG 450. The programmer unit 136 may be controlled by the user (e.g., doctor, clinician) through the user interface 130 allowing the user to interact with the IPG 450. The user interface 130 may permit the user to move electrical stimulation along and/or across one or more of the DBS lead(s) 410 using different DBS electrode 411a-d combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the programmer unit 136 may permit operation of the IPG 450 according to one or more stimulation programs to treat the patient's disorder(s) (e.g., AD). Each stimulation program may include one or more sets of stimulation parameters of the DBS pulse including pulse amplitude, pulse width, pulse frequency or inter-pulse period, pulse repetition parameter (e.g., number of times for a given pulse to be repeated for respective stimset during execution of program), biphasic pulses, monophasic pulses, etc. The IPG 450 modifies its internal parameters in response to the control signals from the programmer unit 136 to vary the stimulation characteristics of the stimulation pulses transmitted through the DBS lead 410 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 5:
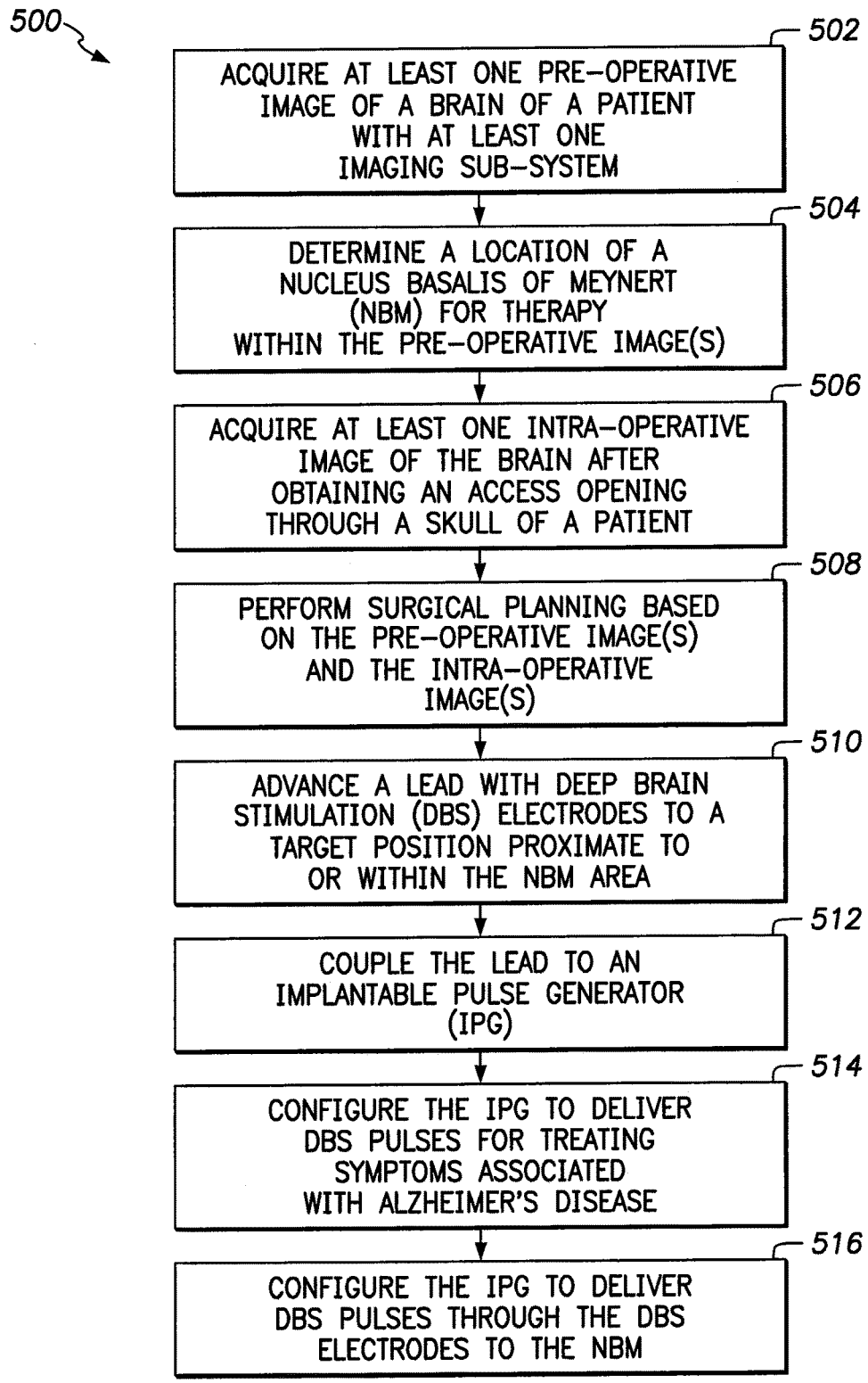
FIG. 5 illustrates a flowchart of a method for performing DBS therapy in accordance with an embodiment of the present disclosure.

FIG. 5 is a flowchart illustrating a method 500 of performing deep brain stimulation (DBS) therapy. The method 500, for example, may employ structures or aspects of various embodiments (e.g., systems and/or methods) discussed herein. For example, the lead may be similar to the DBS lead 410 (FIG. 4) or may include other features, such as those described or referenced herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of performing DBS therapy. It should be noted, other methods may be used.

The method 500 includes acquiring (at 502) at least one pre-operative image of a brain of the patient with at least one imaging sub-system, and determining (at 504) a location of a Nucleus Basalis of Meynert (NBM) for therapy within the pre-operative image(s). For example, the pre-operative image of the brain of the patient 120 may be acquired from the imaging sub-system 104 (e.g., MRI) before surgically implanting, for example, the implantable DBS system 304. The imaging sub-system 104 may receive an instruction to acquire the pre-operative image from the user (e.g., doctor, nurse) directly or through the SP workstation 102 through the I/O interface 132. The SP workstation 102 may receive the pre-operative image from the imaging sub-system 104 through an input of the I/O interface 132. The registration module 118 may register the pre-operative image with a predetermined brain structure atlas, such as a Talairach atlas, to aid the user in determining the location of the DBS target, for example, the NBM. Optionally, the user may select the brain structure atlas and DBS target from the user interface 130. The display module 118 may receive the registered pre-operative image from the registration module 118 and configure the pre-operative image to be displayed or viewed on the display 112.

Additionally or alternatively, the display module 112 may overlay a marker or graphic on the pre-operative image when displayed on the display 112 identifying the DBS target. For example, the pre-operative image is registered with a Montreal Neurological Institute (MNI) atlas by the registration module 118 allowing structures to be located using MNI coordinates. The user may select the DBS target as the NBM or MNI coordinates representing the location of the NBM. The display module 112 may overlay the marker or graphic identifying the location of the coordinates representing the NBM.

In an embodiment, prior to the pre-operative image, anatomical markers may be positioned on the head of the patient 120 to assist in accurately registering the image with the brain structure atlas or subsequent images (e.g., intra-operative image(s)) of the patient 120. The anatomical markers may be placed on a cortical surface of the patient 120.

Figure 6:
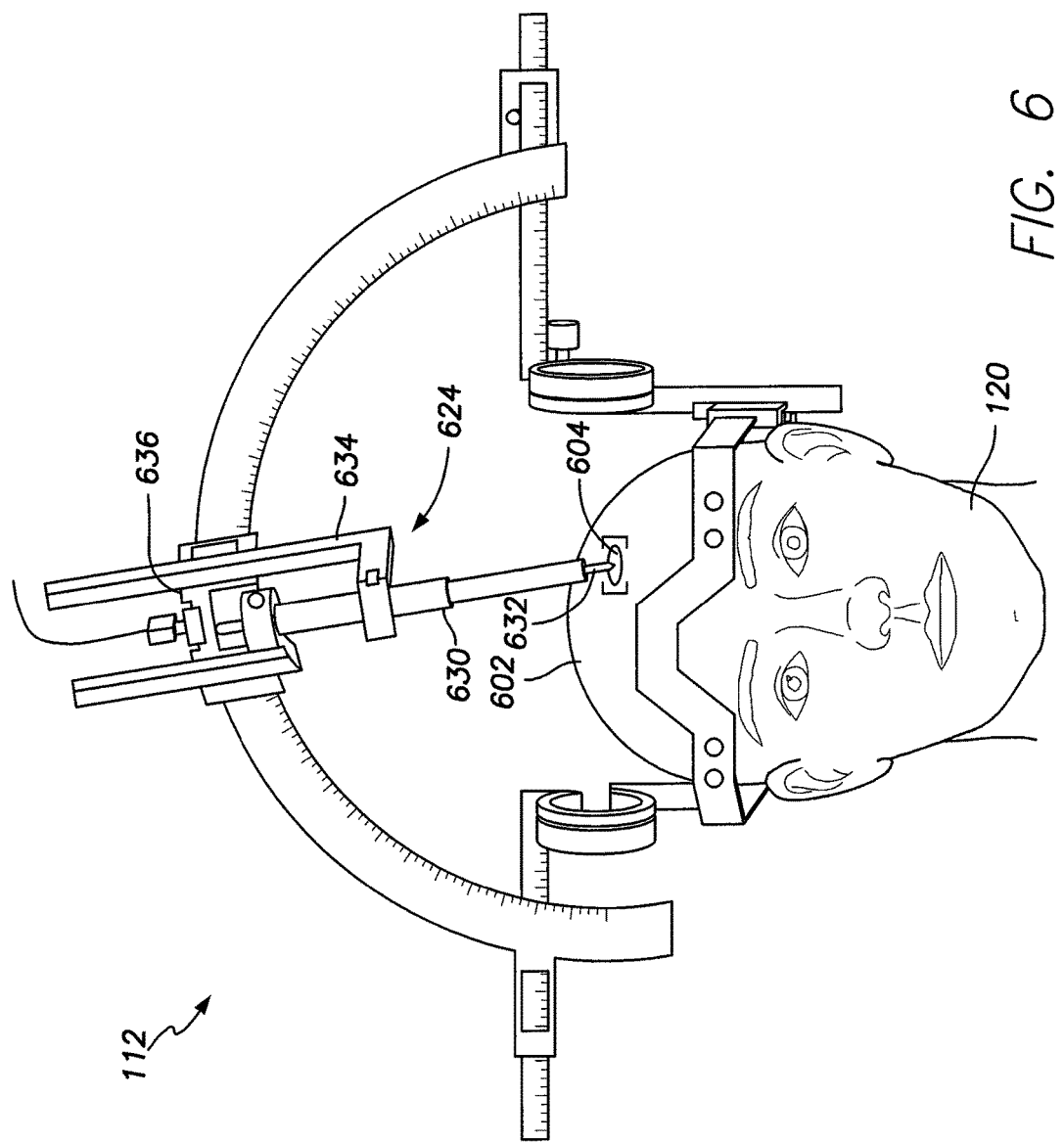
FIG. 6 illustrates a simplified diagram of a surgical drill being used in conjunction with a stereotactic frame to drill a bore hole through a skull of a patient, according to an embodiment of the present disclosure

The method 500 includes acquiring (at 506) at least one intro-operative image of the brain after obtaining an access opening 604 through a skull 602 of the patient 120. For example, FIG. 6 illustrates a simplified diagram of a surgical drill 624 being used in conjunction with the stereotactic frame 122 to obtain the access opening (e.g., bore hole) 604 through the skull 602 of the patient 120, according to an embodiment of the present disclosure. The location of the access opening 604 may be determined through the pre-operative image. The surgical drill 624 may include a main housing 630 operatively connected to a drill bit 632 that is guided into position through one or more guide members 634 and 636 of the stereotactic frame 122. Additionally or alternatively, the surgical drill 624 may be secured to the platform 252. Once in position, the surgical drill 624 is operated to form the access opening 604 through the skull 602. The size of the access opening 604 may be large enough to allow the probe 128 to be advanced into position (e.g., proximate to the DBS target, within the DBS target). Optionally, the surgical drill 624 may be operatively coupled to the control unit 116 allowing the user to operate the surgical drill 624 through the user interface 130. The access opening 604 may be formed through the skull 602 to expose the cortex of the brain.

Figure 7:
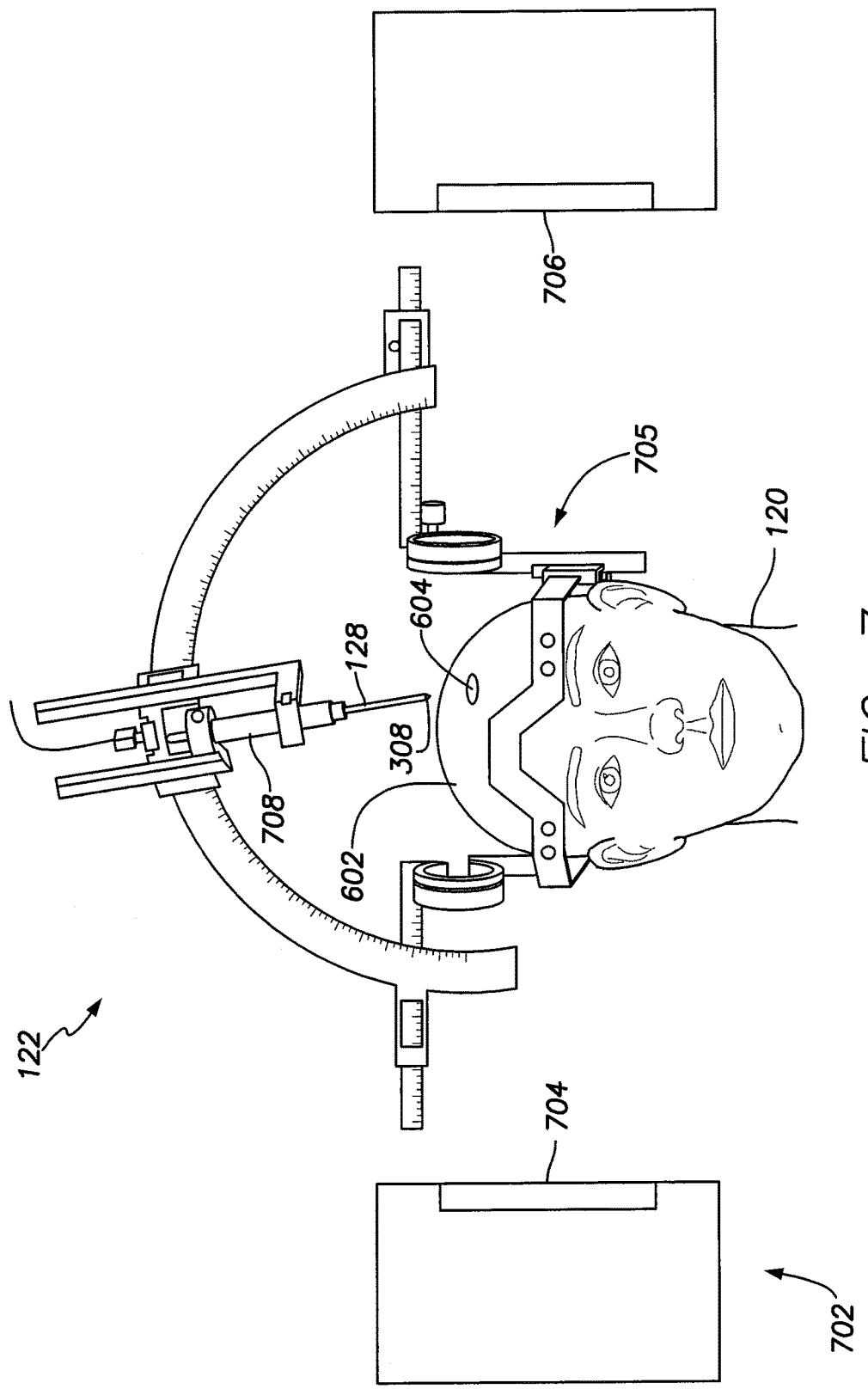
FIG. 7 illustrates a simplified diagram of a patient with a secured stereotactic frame being imaged by an imaging subsystem, according to an embodiment of the present disclosure.

Once the access opening 604 is formed, the surgical drill 624 may be removed from the stereotactic frame 122. FIG. 7 illustrates a simplified diagram of the patient 120 with the secured stereotactic frame 122 being imaged by an imaging sub-system 702 (e.g., CT scanner), according to an embodiment of the present disclosure. For example, the imaging sub-system 702 may be connected to the SP workstation 102 through the I/O interface 132. The head of the patient 120, with the access opening 604, is positioned within an imaging area 705 located between an emitter 706 and a detector 704. The imaging sub-system 702 may receive an instruction to acquire the intra-operative image from the user (e.g., doctor, nurse) directly or through the SP workstation 102 through the I/O interface 132. The SP workstation 102 may receive the intra-operative image from the imaging sub-system 702 through an input of the I/O interface 132. Additionally or alternatively, the imaging sub-system 702 may acquire additional intra-operative images of the head of the patient 120. Optionally, the imaging sub-system 702 may be the same imaging sub-system 104 shown in FIG. 1 and described above.

Figure 8A:
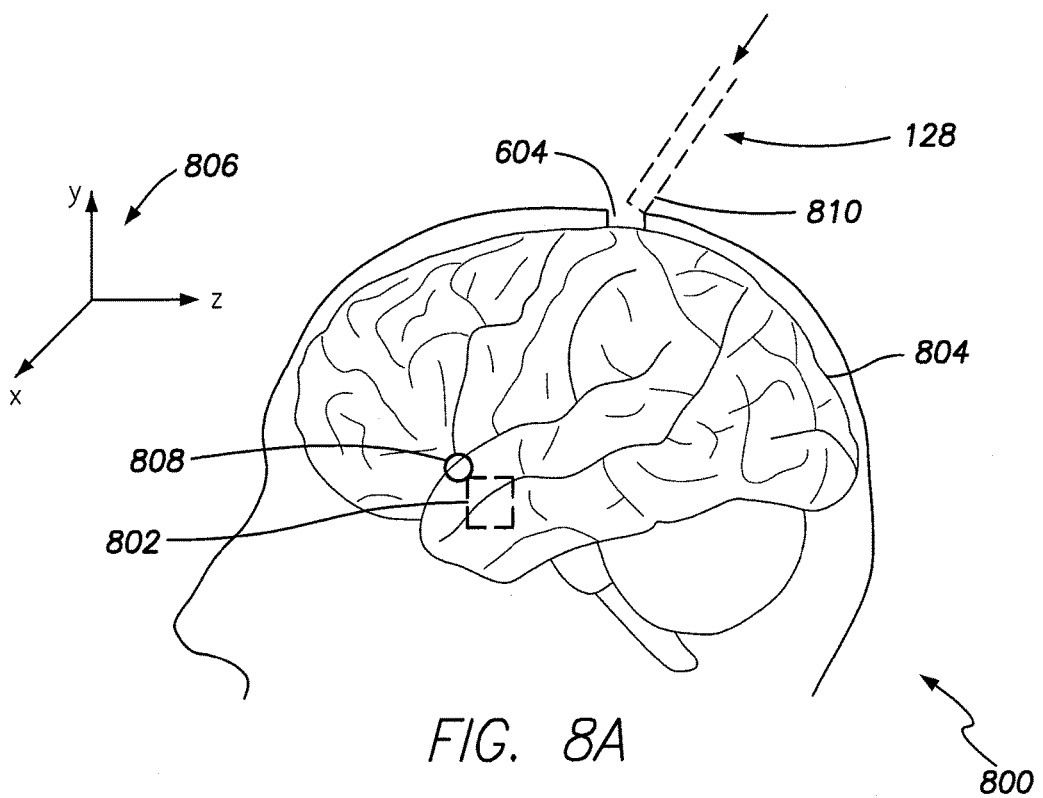
FIG. 8a illustrates a merged image of the pre-operative image and intra-operative image shown on a display, according to an embodiment of the present disclosure.

The method 500 includes performing (at 508) surgical planning based on the pre-operative image(s) and the intra-operative image(s). For example, once the SP workstation 102 receives the intra-operative image, from the image sub-system 702, the registration module 118 may register and/or merge the pre-operative image with the intra-operative image to determine implant coordinates for the DBS lead 410. Optionally, the registration module 118 may register the merged image of the pre-operative image with a brain atlas. FIG. 8a illustrates a merged image 800 of the pre-operative image and intra-operative image as displayed on the display 112, according to an embodiment of the present disclosure. The merged image 800 may include a graphic or mark 802 indicating the location of the DBS target, such as the NBM. The merged image 800 may also indicate the location of the access point 604 and the location of the probe 128 external to the head of the patient 120. Additionally, the merged image 800 may display numeral coordinates of the DBS target and the access point 604 as Cartesian coordinates based on the axes 806 (e.g., latero-lateral axis (x), dorso-ventral axis (y), rostro-caudal axis (z)) and/or based on the brain structure atlas that may be registered with the merged image 800. Alternatively, the coordinates may be based on a polar coordinate system.

Optionally, the merged image 800 may indicate the predetermined implantation distance from the DBS target or implant coordinates 808 of the DBS lead 410. The predetermined implantation distance or implant coordinates 808 may be based on the effective range of the DBS pulses emitted from the DBS electrodes 411*a*-*d* to stimulate the DBS target. The effective range of the DBS pulse may be based on the amplitude of the DBS pulse and the distance between the surface area of the DBS target and the DBS electrodes 411*a*-*d*. It should be noted that as the DBS pulses traverses through the surrounding tissue of the DBS lead 410 away from the DBS electrodes 411*a*-*d*, the amplitude of the DBS pulse decreases due to the resistance of the surrounding tissue. The change in the DBS pulse amplitude may reduce the effectiveness of the DBS pulse in stimulating the DBS target. For example, the DBS pulses emitted from the DBS electrodes 411*a*-*d* may be configured to have a pulse amplitude of 10 milli-amperes (mA). Preferably, the DBS target may be within 5.0 mm of the DBS electrodes 411*a*-*d* to effectively stimulate the DBS target by the DBS pulse. It should be noted, that increasing the DBS pulse amplitude may increase the effective distance available as an option between the DBS electrodes 411*a*-*d* and the DBS target to effectively stimulate the DBS target. Conversely, when the DBS pulse amplitude is decreased the effective distance to stimulate the DBS target also decreases. For example, the DBS pulse having a pulse amplitude of 1 mA would preferably be closer to the DBS target relative to a DBS pulse having a pulse amplitude of 10 mA.

Figure 8B:
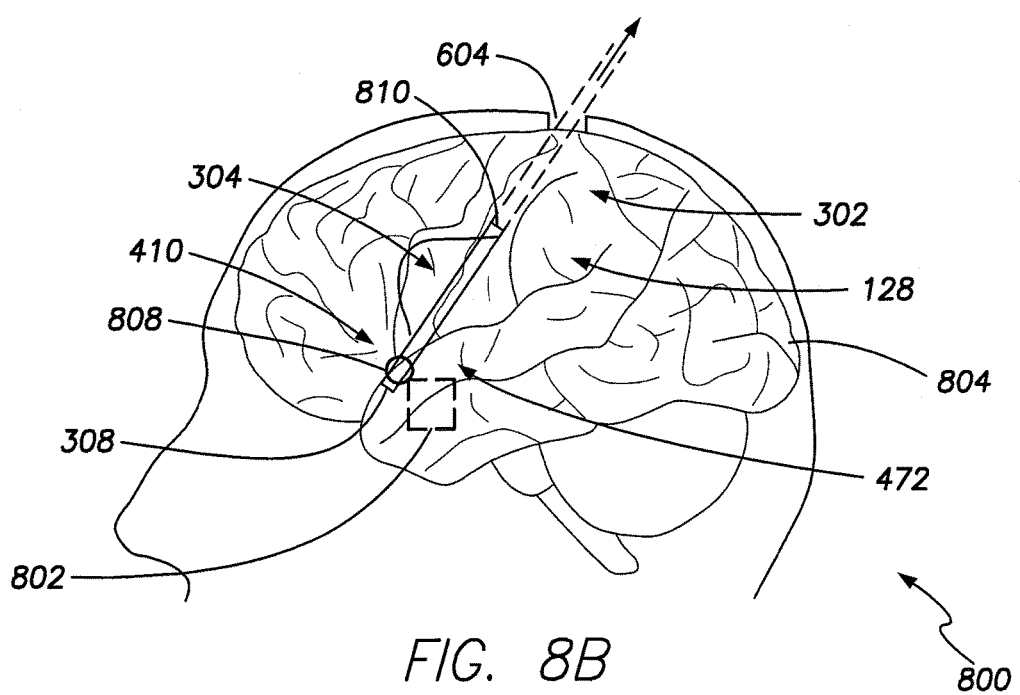
FIG. 8b illustrates a merged image of the pre-operative image and intra-operative image shown on a display, according to an embodiment of the present disclosure.

The method 500 includes advancing (at 510) the DBS lead 410 with the deep brain stimulation (DBS) electrodes 411*a*-*d* to the target position (e.g., implant coordinates 808) proximate to or within the NBM area 802. For example, the probe 128 may be guided into the skull 602 of the patient 120 by the stereotactic frame 122 (shown in FIG. 7). A driving mechanism 708, controlled by the control unit 116, may advance the probe 128 into the skull 602 of the patient. As shown in FIG. 8*a*, the distal end of the probe 128, proximate to the brain 804, may include a radiopaque fiducial 810. The radiopaque fiducial 810 may be used to register and/or track a position of the probe 128 as the probe 128 advances within the brain 804. Once the distal end or the radiopaque fiducial 810 reaches the implant coordinates 808, the DBS lead 410 and the DBS lead body 472 may be advanced through the guide tube 302 by the driving mechanism. The radiopaque fiducial 308, similar to the radiopaque fiducial 810, may be used to track a position of the DBS lead 410 as the radiopaque fiducial 308 advances through the guide tube 302 destine for the implantation coordinates 808. Once the distal end or the radiopaque fiducial 308 reaches the implantation coordinates 808, as shown in FIG. 8*b*, the guide tube 302 may be removed leaving the DBS lead 410 with the DBS electrodes 411*a*-*d* and the DBS lead body 472 in position. Optionally, the radiopaque fiducial 308 at the distal end of the DBS lead 410 or the DBS lead 410 alone may be tracked in subsequent intra-operative image(s) to monitor any post implantation displacement or to confirm the DBS lead 410 is implanted within the implantation coordinates.

Figure 9A:
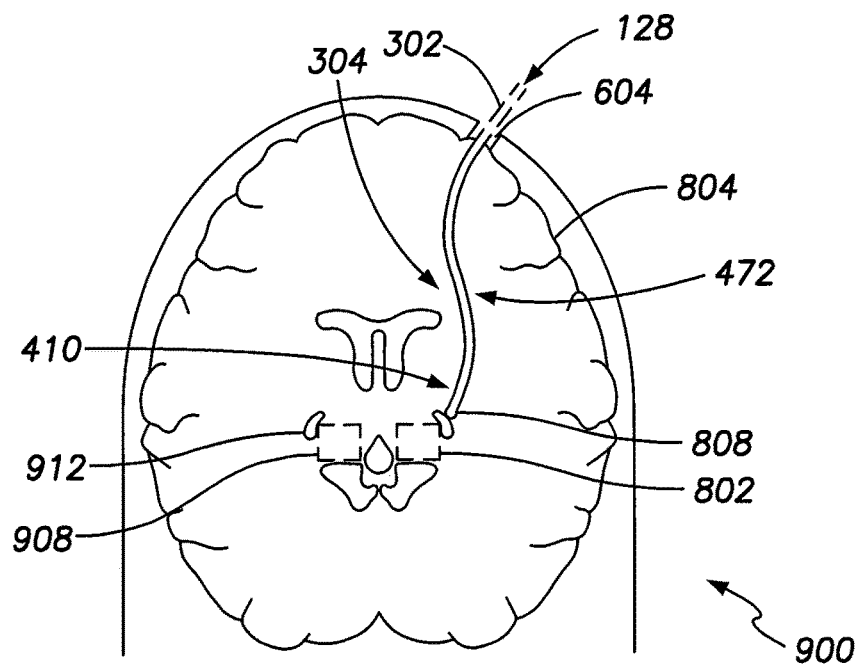
FIG. 9a illustrates the merged image of FIG. 8b from a coronal shown on a display, according to an embodiment of the present disclosure.
Figure 9B:
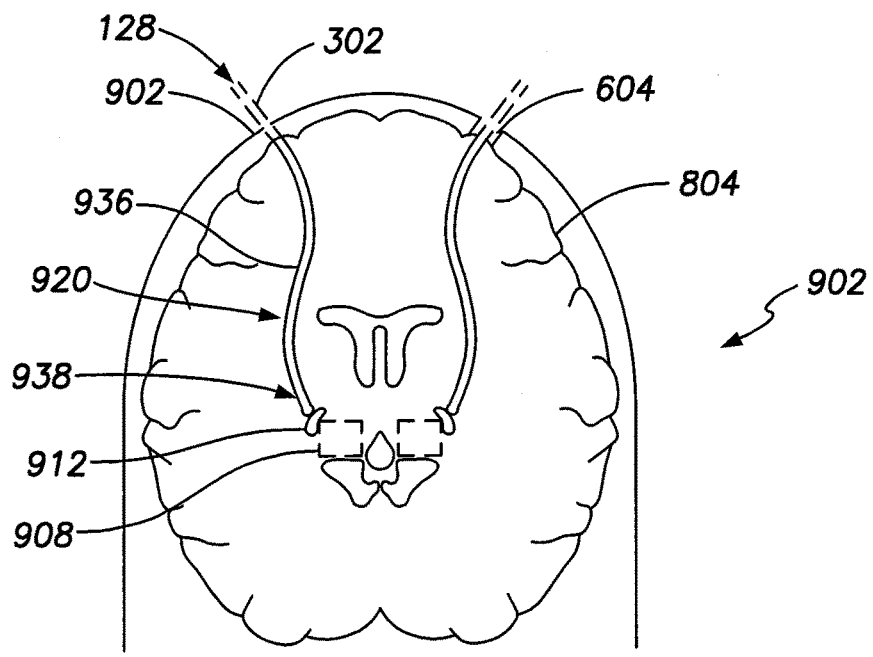
FIG. 9b illustrates the merged image of FIG. 8b from a coronal shown on a display, according to an embodiment of the present disclosure.

It should be noted, that even though a single DBS lead 410 is described being implanted into the patient 120 in other embodiments, a plurality of DBS leads 410 and 938 may be advanced into a plurality of different implantation coordinates 808 and 912. FIG. 9*a* illustrates a coronal plane merged image 900 (parallel to the latero-lateral axis (x)) from the merged image 800 of patient 120 shown in FIG. 8*b*. However, the merged image 900 may also include an additional implantation coordinate 912 proximate to or within an alternative DBS target location. The alternative DBS target location may be a second NBM area 908. FIG. 9*b* illustrates a second DBS lead 938 advanced into position through the guide tube 302, using the method described above, as the guide tube 302 is being removed through a second access point 902. Optionally, the same access point (e.g., access point 604) may be used to advance the first and second DBS leads 410 and 938 to the implantation coordinates 808 and 912, respectively.

The method 500 includes coupling (at 512) the DBS lead 410 to the implantable pulse generator (IPG) 450. For example, as described above, the IPG 450 may be electrically coupled to the DBS lead 410 through conductors from the IPG header through the DBS lead body 472 to the DBS lead 410.

The method 500 includes configuring (at 514) the IPG 450 to deliver DBS pulses for treating symptoms associated with AD and configuring (at 516) the IPG to deliver DBS pulses through the DBS electrodes to the NBM. For example, as described above, the IPG 450 may be programmed by the programmer unit 136 to emit DBS pulses from the DBS electrodes 411*a*-*d* in accordance with a stimulation program for treating AD symptoms (e.g., impairment of cognitive functions) by stimulating the NBM.

Figure 10:
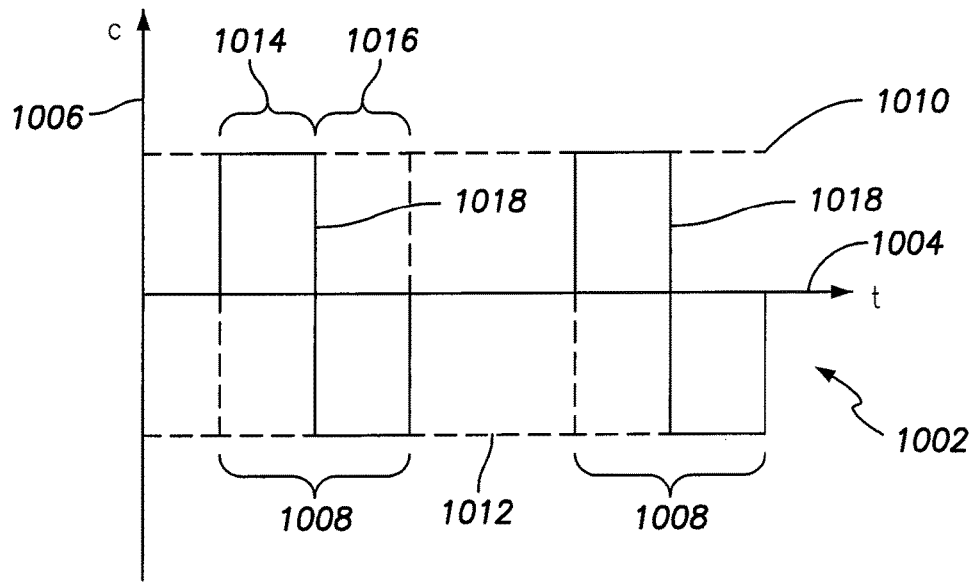
FIG. 10 graphically illustrates of a DBS pulse, according to an embodiment of the present disclosure.

FIG. 10 illustrates a graphical representation of a DBS pulse 1002 emitted from at least one of the DBS electrodes 411*a*-*d* with a surface area proximate to the NBM to stimulate or increase acetylcholine (Ach) levels, which improves cognitive functions (a symptom of AD). Optionally, in alternative embodiments the surface area of the DBS electrodes 411*a*-*d* may be within the NBM. The vertical axis 1006 represents current or the flow of electric charge from the DBS electrode 411*a*-*d* to the surrounding tissue (e.g., the NBM). The horizontal axis 1004 represents time. The DBS pulse 1002 is shown as a biphasic pulse with a positive current amplitude 1010 and a negative current amplitude 1012 within a set pulse width 1008. The differing current amplitudes may be dependent on a state, specifically a cathode or anode state of the DBS electrode 411*a*-*d*.

For example, the DBS pulse 1002 is emitted from the DBS electrode 411*a* of the DBS lead 410. The DBS electrode 411*a* may receive the DBS pulse 1002 from the IPG 450 through the electrical conductors of the IPG header and the DBS lead body 472 in accordance with the stimulation program. The stimulation program may determine that the DBS pulse 1002 may have a pulse width 1008 of 150 microseconds (μsec) and an amplitude 1010 of 10 mA. The pulse width 1008 of the DBS pulse 1002 is separated into two transition phases an anode phase 1014 and a cathode phase 1016. Each of the phases 1014 and 1016 may be approximately 75 μsec in length. To create the biphasic pulse the IPG 450, through the switching circuitry 457, may transition the DBS electrode 411*a* between the anode and cathode state. During the anode state the DBS electrode 411a may be electrically coupled via the switching circuitry 457 to an energy storage device, such as a capacitor or battery. Thereby, the DBS electrode 411a may emit electric charge radially outward toward the NBM at the positive current amplitude 1010 during the anode phase 1014.

Conversely, during the cathode state the DBS electrode 411a may be electrically coupled via the switching circuitry 457 to ground or a ground plane. Thereby, the DBS electrode 411a may receive electric charge from surrounding tissue or adjacent DBS electrodes 411b-d that are emitting electric charge shown as the negative current amplitude 1012 during the cathode phase 1016. It should be noted that a transition 1018 between the anode and cathode phases 1014 and 1016 is shown in FIG. 10 as a vertical line (e.g., instantaneous switching), however, in other embodiments the transition 1018 may be a period of time greater than zero.

It should again be noted that the above electrical specifications (e.g., type of pulse, amplitude, frequency, and other electrical characteristics) are for illustrative purposes only. In alternative embodiments the electrical specifications may be greater than or lower than described above/below. For example, the pulse width 1008 may be greater (e.g., 200 μsec) than or lesser (e.g., 50 μsec, 75 μsec) than described above.

Figure 11:
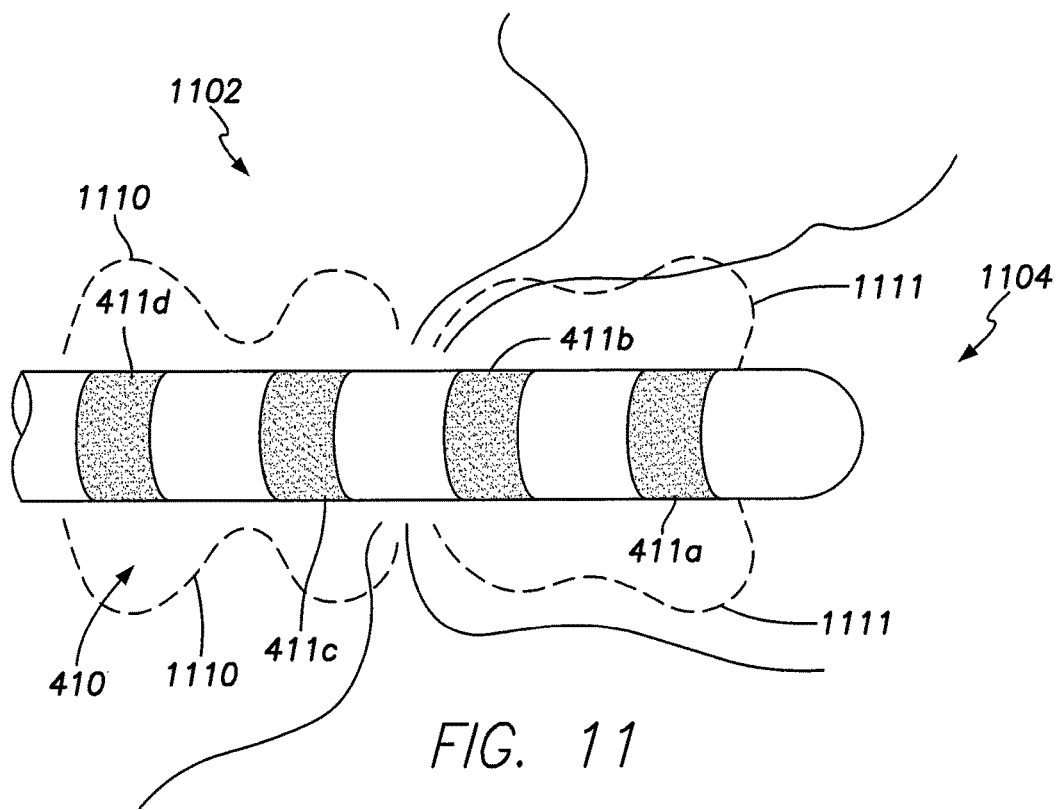
FIG. 11 illustrates a DBS lead proximate to a Nucleus Basilis of Meynert and a Nucleus Accumbens, according to an embodiment of the present disclosure.

Optionally, a DBS lead may be positioned to deliver DBS pulses to multiple DBS targets, such as both of the NBM and the Nucleus Accumbens (NAcc). As described above, the NAcc is positioned adjacent to the NBM and may be stimulated to treat psychiatric symptoms such as depression, anhedonia, and anxiety, which may be additional symptoms of patients suffering from AD. FIG. 11 illustrates the DBS lead 410 positioned at implantation coordinates such that the surface area of the DBS lead 410 is proximate to both of the DBS targets, such as the NBM 1104 and the NAcc 1102. Optionally, the implantation coordinates may be within the DBS targets such that the DBS lead 410 may be positioned within the NBM 1104 and the NAcc 1102. The position of the DBS lead 410 allows two sets or combinations of DBS electrodes, the DBS electrodes 411c-d and the DBS electrodes 411a-b, to have energy trajectories 1110 and 1111 overlap the NAcc 1102 and NBM 1102, respectively. The energy trajectories 1110 and 1111 may represent an area or distance from the DBS electrodes 411c-d and 411a-b, respectively, to the NAcc 1102 and NBM 1102 that a DBS pulse emitted from the DBS electrodes 411c-d and 411a-b may be propagated through the surrounding tissue and stimulate the NAcc 1102 and the NBM 1102. The area or distance from energy trajectories 1110 and 1111 may be increased or decreased by adjusting the amplitude of the DBS pulse, as described above.

Figure 12:
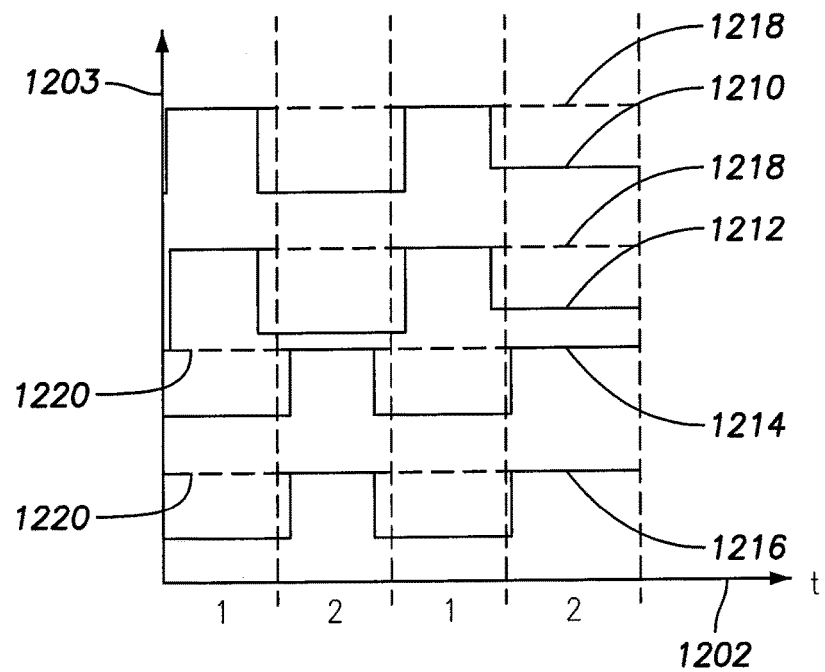
FIG. 12 graphically illustrates DBS pulses, according to an embodiment of the present disclosure.

FIG. 12 illustrates a graphical representation of DBS pulses 1210, 1212, 1214, and 1216 emitted from the DBS electrodes 411a-d, respectively. The DBS pulses 1210 and 1212 represent the set of DBS electrodes 411a-b that stimulate the NBM 1104. The DBS pulses 1214 and 1216 represent the set of DBS electrodes 411c-d that stimulate the NAcc 1102. The vertical axis 1203 represents a current amplitude. The horizontal axis 1202 represents time and is divided into two different time periods, '1' and '2'. Each time period corresponds to a different state for each set of DBS electrodes 411a-d. The two different time period allow the NBM and the NAcc to receive DBS therapies or DBS pulses intermittently.

For example, during the time period '1', the IPG 450 may configure or set the DBS electrodes 411a-b through the switching circuitry 457 to the anode state. Thereby the DBS electrodes 411a-b emit DBS pulse amplitudes 1218 stimulating the NBM 1104. It should be noted that during the time period '1', the DBS electrodes 411c-d may be configured by the IPG 450 in an open or inactive state such that the DBS electrodes 411c-d are not emitting energy (e.g., the DBS pulse). During the time period '2', the IPG 450 may configure or set the DBS electrodes 411a-b through the switching circuitry 457 to the open or inactive state. Thereby, the NBM 1104 is no longer stimulated by the DBS electrodes 411a-b. Conversely, the IPG 450 may configure or set the DBS electrodes 411c-d through the switching circuitry 475 to the anode state. Thereby, the DBS electrodes 411c-d emit the DBS pulse amplitudes 1220 stimulating the NAcc 1102. It should be noted that even though the DBS pulses 1210, 1212, 1214, and 1216 are illustrated as monophasic pulses other pulse configurations are possible within the time periods '1' and '2', such as biphasic pulses. Optionally, additional time period may be used based on alternative stimulation programs used in different embodiments.

Figure 13:
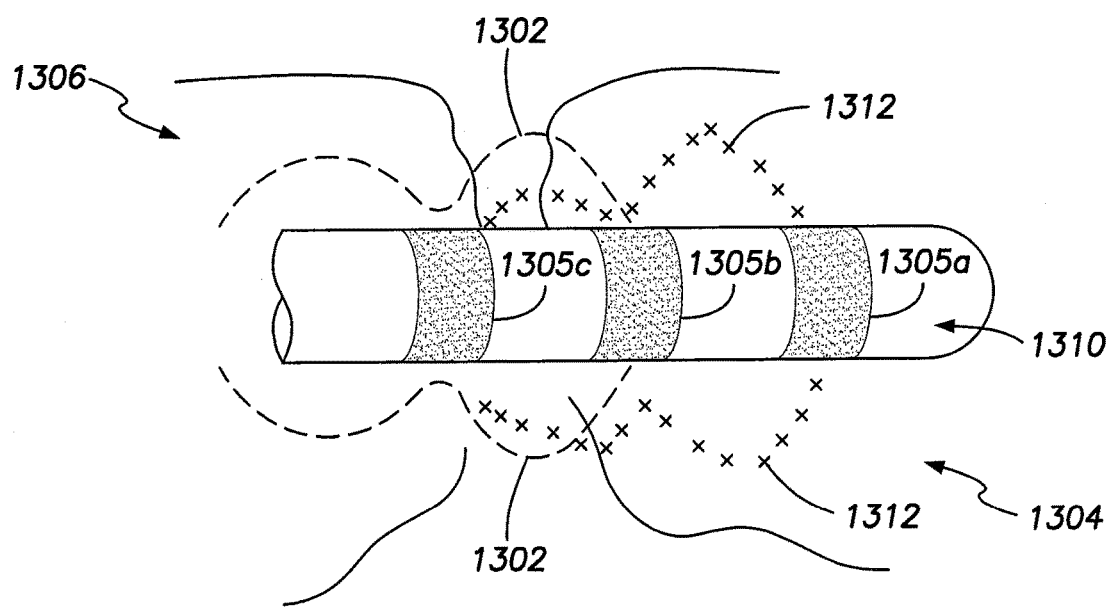
FIG. 13 illustrates a DBS lead proximate to a Nucleus Basilis of Meynert and a Nucleus Accumbens, according to an embodiment of the present disclosure.

Optionally, as shown in FIG. 13, a DBS lead 1310 may be positioned such that DBS electrodes 1305a-c may be divided into two sets or combination of DBS electrodes 1305a-b and 1305b-c with a common DBS electrode 1305b. Each set of DBS electrodes 1305a-b and 1305b-c have energy trajectories 1312 and 1302, respectively, that may stimulate two different DBS targets, such as NBM 1304 and NAcc 1306.

Optionally, the IPG 450 may be programmed or configured by the programmer unit 136 to deliver DBS pulses or stimulate DBS targets through the DBS electrodes 411a-d to manage or slow down a progression of AD.

Optionally, the IPG 450 may be programmed or configured by the programmer unit 136 to deliver DBS pulses or stimulate DBS targets through the DBS electrodes 411a-d in a current regulated and/or charge balance manner.

Optionally, the performing of DBS therapy may include maintaining parameters associated with the DBS pulse constant for an extended wait period of time while testing for a present of acute or sub-acute side effect (e.g., dysfunctional illumination, hearing issues, or the like), following the wait period of time adjusting the parameters.

For example, the DBS lead 410 is implanted within the implantation coordinates and coupled to the IPG 450. Once implanted, the user may perform a testing sequence emitted from the DBS electrodes 411a-d as DBS pulses. The testing sequence may be initiated by the user using the user interface 130, which communicates to the programmer unit 136. The IPG 450 may receive the testing sequence instructions from the programmer unit 136 with predetermined DBS pulses that are emitted from the DBS electrodes 411a-d. During the testing sequence, the user or doctor may test the eye sight of the patient to determine if the patient is experiencing dysfunctional illumination or see flashes while the DBS pulses are emitted from the DBS electrodes 411a-d. Dysfunctional illumination may occur when the DBS lead 410 is implanted incorrectly with respect to the NBM and will need to be moved.

Optionally, the performing of DBS therapy may include performing a global measure of cognitive function that include tests for at least one of declarative memory, orientation, praxis, receptive language or expressive language. For example, post implantation of the DBS lead 410 the doctor may perform a series of examinations of the patient to consciously recall facts, knowledge and/or past experiences of the patient to test the declarative memory of the patient. Based on the examination results, the doctor may alter or modify the DBS pulses (e.g., frequency, amplitude, state sequences) through the user interface 130 by reprogramming the IPG 450 through the programmer unit 136.

The modules 106 and 118, the programmer unit 136, the IPG 450, and control unit 116 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules 106 and 118, the programmer unit 136, the IPG 450, and control unit 116 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The modules 106 and 118, the programmer unit 136, the IPG 450, and control unit 116 may execute a set of instructions that are stored in one or more storage elements, in order to process data. The storage elements may also store data or other information as desired or needed. The storage element may be in the form of an information source or a physical memory element within the modules 106 and 118, the programmer unit 136, the IPG 450, and control unit 116. The set of instructions may include various commands that instruct the modules 106 and 118, the programmer unit 136, the IPG 450, and control unit 116 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for performing deep brain stimulation (DBS) therapy, the method comprising:
   pre-operatively acquiring at least one pre-operative image of a brain of a patient with at least one imaging sub-system;
   determining a location of a Nucleus Basalis of Meynert (NBM) for therapy in the at least one pre-operative image;
   infra-operatively acquiring at least one intra-operative image of the brain after obtaining an access opening through a skull of the patient;
   performing surgical planning based on the pre-operative image and the intra-operative image;
   advancing a lead having deep brain stimulation (DBS) electrodes to a target position proximate to or within the NBM area;
   coupling the lead to an implantable pulse generator (IPG) configured to deliver DBS pulses through the DBS electrodes to the NBM, the IPG to deliver DBS pulses for treating symptoms associated with Alzheimer's Disease (AD); and
   wherein the surgical planning and advancing operations locate the DBS electrodes such that a Nucleus Accumbens (NAcc) and the NBM are both located within an energy trajectory of the DBS delivered by, and propagating from, the DBS electrodes.

2. The method of claim 1, wherein the target position is proximate to the NBM area such that a surface of the DBS electrodes is within 5.0 mm of the NBM.

3. The method of claim 1, wherein the advancing operation further comprises bilaterally advancing first and second leads to first and second target positions that are proximate to or within first and second NBM areas, respectively.

4. The method of claim 1, further comprising configuring the IPG to deliver a stimulation therapy that includes at least one of biphasic pulses having a pulse width of 50-150 usec and pulses having an amplitude of 1.0 to 10.0 mA.

5. The method of claim 1, further comprising delivering an NBM therapy utilizing a first combination of DBS electrodes to the NB M area, and delivering a Nucleus Accumbens (NAcc) therapy utilizing a second combination of DBS electrodes to a NAcc area, the first and second combination of DBS electrodes having at least one different electrode.

6. The method of claim 1, further comprising the IPG configuring the DBS electrodes on the lead into first and second electrode sets, such that 1) at one point in time, the IPG setting the first electrode set in a STIM ON state in which the first electrode set deliver CGS pulses for a first period of time to the NB M area, while the second electrode set is in a STIM OFF state, and 2) at a second point in time, the IPG setting the second electrode set in a STIM ON state in which the second electrode set delivery DBS pulses for a second period of time to a Nucleus Accumbens (NAcc) area, while the first electrode set is in the STIM OFF state.

7. The method of claim 1, further comprising configuring the IPG to deliver a first DBS therapy directed toward the NBM and a second DBS therapy directed toward a Nucleus Accumbens (NAcc), the first and second DBS therapies being delivered intermittently.

8. The method of claim 1, further comprising maintaining parameters associated with the DBS pulses constant for an extended wait period of time while testing for a presence of acute or sub-acute side effects, following the wait period of time adjusting the parameters.

9. The method of claim 1, further comprising performing a global measure of cognitive function that includes tests for at least one of declarative memory, orientation, praxis, receptive language or expressive language.

10. A system for performing deep brain stimulation (DBS) therapy, the system comprising:
    a surgical planning (SP) work station having an input configured to receive at least one pre-operative image of a brain of a patient with at least one imaging sub-system;
    the SP work station configured to permit a user to determine a location of a Nucleus Basalis of Meynert (NBM) for therapy in the at least one pre-operative image;
    the SP work station having an input configured to receive at least one intra-operative image of the brain after obtaining an access opening through a skull of the patient;
    the SP work station configured to perform surgical planning based on the pre-operative image and the intra-operative image;
    a lead having deep brain stimulation (DBS) electrodes on the lead, the DBS electrodes configured to be advanced to a target position proximate to or within the NBM area;
    an implantable pulse generator (IPG) coupled to the lead, the IPG configured to deliver DBS pulses through the DBS electrodes to the NBM, the implantable pulse generator configured to deliver DBS pulses for treating symptoms associated with Alzheimer's Disease (AD); and
    wherein the surgical planning and advancing operations locate the DBS electrodes such that a Nucleus Accumbens (NAcc) and the NBM are both located within an energy trajectory of the DBS delivered by, and propagating from, the DBS electrodes.

11. The system of claim 10, wherein the target position is proximate to the NBM area such that a surface of the DBS electrodes is within 5.0 mm of the NBM.

12. The system of claim 10, further comprising first and second leads bilaterally advanced to first and second target positions that are proximate to or within first and second NBM areas, respectively.

13. The system of claim 10, wherein the IPG is further configured to deliver a secondary DBS therapy directed toward a Nucleus Accumbens (NAcc) for treating psychiatric symptoms.

14. The system of claim 10, wherein the IPG is further configured to deliver a stimulation therapy that includes at least one of biphasic pulses having a pulse width of 50-150 usec and pukes having an amplitude of 1.0 to 10.0 mA.

15. The system of claim 10, wherein the IPG is further configured to deliver an NBM therapy utilizing a first combination of DBS electrodes to the NPM area, and deliver a Nucleus Accumbens (NAcc) therapy utilizing a second combination of DBS electrodes to a NAcc area, the first and second combination of DBS electrodes having at least one different electrode.

16. The system of claim 10, wherein the DBS electrodes on the lead are configured into first and second electrode sets, wherein 1) at one point in time, the IPG sets the first electrode set in a STIM ON state in which the first electrode set deliver DBS pukes for a first period of time to the NBM area, while the second electrode set k in a STIM OFF state, and 2) at a second point in time, the IPG sets the second electrode set in a STIM ON state in which the second electrode set delivery DBS pulses for a second period of time to a Nucleus Accumbens (NAcc) area, while the first electrode set is in the STIM OFF state.

17. The system of claim 10, further comprising maintain parameters associated with the DBS pulses constant for an extended wait period of time while testing for a presence of acute or sub-acute side effects, following the wait period of time adjusting the parameters.

18. The system of claim 10, wherein a global measure of cognitive function is performed that includes tests for at least one of declarative memory, orientation, praxis, receptive language or expressive language.

19. A method for performing deep brain stimulation (DBS) therapy, the method comprising:
    pre-operatively acquiring at least one pre-operative image of a brain of a patient with at least one imaging sub-system;
    determining a location of a Nucleus Balsas of Meynert (NBM) for therapy in the at least one pm-operative image;
    intra-operatively acquiring at least one intra-operative image of the brain after obtaining an access opening through a skull of the patient;
    performing surgical planning based on the pre-operative image and the intra-operative image;
    advancing a lead having deep brain stimulation (DBS) electrodes to a target position proximate to or within the NBM area;
    coupling the lead to an implantable pulse generator (IPG) configured to deliver DBS pulses through the DBS electrodes to the NBM, the IPG to deliver DBS pulses for treating symptoms associated with Alzheimer's Disease (AD); and
    delivering an NBM therapy utilizing a first combination of DBS electrodes to the NBM area, and delivering a Nucleus Accumbens (NAcc) therapy utilizing a second combination of DBS electrodes to a NAcc area, the first and second combination of DBS electrodes having at least one different electrode.

20. The method of claim 19, further comprising the IPG configuring the DBS electrodes on the lead into first and second electrode sets, such that 1) at one point in time, the IPG setting the first electrode set in a STIM ON state in which the first electrode set deliver DBS pulses for a first period of time to the NBM area, while the second electrode set is in a STIM OFF state, and 2) at a second point in time, the IPG setting the second electrode set in a STIM ON state in which the second electrode set delivery DBS pulses for a second period of time to a Nucleus Accumbens (NAcc) area, while the first electrode set is in the STIM OFF state.

* * * * *